United States Patent [19]

Jessee et al.

[11] Patent Number: 4,981,797
[45] Date of Patent: Jan. 1, 1991

[54] PROCESS OF PRODUCING HIGHLY TRANSFORMABLE CELLS AND CELLS PRODUCED THEREBY

[75] Inventors: Joel A. Jessee; Fredric R. Bloom, both of Gaithersburg, Md.

[73] Assignee: Life Technologies, Inc., Gaithersburg, Md.

[21] Appl. No.: 273,646

[22] Filed: Nov. 14, 1988

Related U.S. Application Data

[63] Continuation of Ser. No. 763,825, Aug. 8, 1985, abandoned.

[51] Int. Cl.$^5$ .......................... C12N 1/20; C12N 1/21; C12N 15/63; C12N 15/00
[52] U.S. Cl. .................................. 435/172.3; 435/91; 435/170; 435/172.1; 435/252.3; 435/252.8; 435/320; 435/849; 935/52; 935/55; 935/56; 935/58; 935/66; 935/72; 935/73
[58] Field of Search ...................... 435/91, 170, 172.1, 435/172.3, 252.3, 849, 252.8, 320; 935/52, 55, 56, 58, 66, 72, 73

[56] References Cited

U.S. PATENT DOCUMENTS 4,851,348  7/1989  Hanahan .................... 435/252.33

OTHER PUBLICATIONS

Dityatkin et al., *Chem. Abstracts* 89:176192r, 1978.
Dityatkin et al., *Chem. Abstracts* 90:148301c, 1979.
Dityatkin et al., *Chem. Abstracts* 90:183010d, 1979.
Hanahan, D., *J. Mol. Biol.* 166:557–580, 1983.
Morrison, D. A., *Methods Enzymol* 68:326–331, 1979.
Hanahan, D., In: *DNA Cloning* (D. M. Glover, ed) IRL Press, Washington, D.C., pp. 109–135.
Suzuki et al., *Methods Enzymol* 68:331–342, 1979.
Morrison, D. A., *J. Bacteriol* 132(1):349–351, 1977.
Van Die, Im et al., *J. Gen. Micro* 129:663–670, 1983.
Bethesda Research Laboratories Catalogue and Reference Guide, 1985, p. 41.

*Primary Examiner*—Richard A. Schwartz
*Assistant Examiner*—Richard C. Peet
*Attorney, Agent, or Firm*—Saidman, Sterne, Kessler & Goldstein

[57] ABSTRACT

Process for producing transformable, competent cells including the steps of growing the cells in a growth conducive medium at a temperature of less than 37° C. and freezing the cells, and cells produced by the process.

24 Claims, No Drawings

PROCESS OF PRODUCING HIGHLY TRANSFORMABLE CELLS AND CELLS PRODUCED THEREBY

This application is a continuation of application Ser. No. 763,825, filed Aug. 8, 1985, now abandoned.

BACKGROUND OF THE INVENTION

This invention relates to a process for producing cells of improved competency that are transformable ("competency" referring to the ability of cells to take up and establish exogenous DNA), and to such competent cells. This aspect of the invention relates particularly to cells of *Escherichia coli* having competency for plasmid DNA. The invention further relates to such a process and to cells produced by the process, which can be repeatedly frozen and thawed without significant loss in transformability.

The methods used for the insertion of exogenous DNA sequences and genes from a variety of organisms into *Escherichia coli* been described in U.S. Pat. No. 4,237,224 (Cohen and Boyer, 1980). That patent describes the preparation of hybrid plasmid molecules, the insertion of these hybrid plasmid molecules into cells of *E. coli*, and the replication and amplification of these recombinant plasmids in the transformed cells. The extensive use of and interest in recombinant DNA technology has resulted in a great need for *E. coli* cells which are capable of taking up and establishing recombinant plasmid molecules, since competent *E. coli* have become important to the process of introducing and amplifying exogenous genes or sequences.

A number of procedures exist for the preparation of competent *E. coli* cells and the introduction of DNA into these cells. For example Mandel and Higa (1970, Journal of Molecular Biology 53:159) describe a procedure whereby bacteriophage DNA is combined with *E. coli* cells in the presence of 50 mM $Ca^{++}$ at 0° C. followed by a brief heat pulse at 37°–42° C. This method has been extended to the uptake of chromosomal DNA (Cosloy and Oishi 1973, Proceedings of the National Academy of Science 70:84) and plasmid DNA (Cohen et al 1972, PNAS 69:2110). A summary of the factors influencing the efficiency of transformation is given in Hanahan (1983, JMB 166:557). These factors include the addition of other cations such as Mg, Mn, or Rb to the Ca-treated cells as well as the prolonged incubation of the cells in $CaCl_2$. The efficiency of transformation of *E. coli* cells is substantially enhanced by the method described by Hanahan (1983, JMB, hereinafter referred to as "Hanahan (1983)"). The *E. coli* cells are grown at 37° C. in the presence of 20 mM Mg. Plasmid DNA is combined with the cells at 0° C. in the presence of Mn, Ca, Rb or K, dimethylsulfoxide (DMSO), dithiothreitol (DTT) and hexamine cobalt chloride.

Several *E. coli* strains prepared by the latter method have transformation efficiencies of from 1 to $5 \times 10^8$ transformants/ug plasmid DNA. Generally frozen competent cells have transformation efficiencies of about $1 \times 10^8$ transformants/ug plasmid DNA. These competent cells can be stored frozen at −70° C. for several months without significant loss of transformation efficiency. However, the foregoing frozen cells cannot be thawed and refrozen without significant loss of transformation efficiency.

SUMMARY OF THE INVENTION

It is an object of the present invention to provide cells of improved competency.

It is a further object of the invention to provide highly competent cells that have high transformation efficiencies.

Another object of the invention is the provision of competent, highly transformable cells that can repeatedly be frozen and thawed without significantly reducing their transformability.

An additional object is to provide highly competent, highly transformable *E. coli* cells.

Yet another object is to provide a process for making cells of improved competency.

It is a further object of the invention to provide a process for producing highly competent cells that are transformable.

Another object is the provision of a process for producing competent cells that are highly transformable, and that can repeatedly be frozen and thawed without significant reductions in competency.

It is still a further object to provide a process for producing highly transformable *E. coli* of improved competency.

Other objects will be apparent from the description to follow and from the appended claims.

The present invention in its preferred forms provides processes for the preparation of frozen competent *E. coli* cells having transformation efficiencies greater than $5 \times 10^8$ transformants per ug plasmid DNA, generally greater than $10^9$ transformants/ug plasmid DNA. These cells have the useful property of being capable of being repeatedly frozen and thawed without substantial loss of transformation efficiency.

DETAILED DESCRIPTION OF THE PREFERRED EMBODIMENTS

The processes described below involve the growth of *E. coli* cells in a growth conducive medium such as a complex medium containing Mg at temperatures of less than 37° C., and generally between 18°–32° C. for a time period of between 1–20 hours, or until the optical density ("O.D.") of the culture at 550 nm reaches 0.5–1.0, washing the cells in a buffer containing 10 mM potassium acetate, 100 mM KCl, 45 $MnCl_2.4H_2O$, 10 mM $CaCl_2.2H_2O$, 3 mM hexamine cobalt chloride, and 10% redistilled glycerol according to the procedure of Hanahan (1983), incubating cells with DMSO and freezing the cells in a dry ice-ethanol bath and storing the cells at −70° C. Growth of the cells at temperatures between 18° C. and 32° C. as well as the subsequent freezing step are both essential to the process of preparing highly competent *E. coli* cells with the property of being repeatedly frozen and thawed without substantial loss of transformation efficiency. The *E. coli* strains prepared according to the method described below are useful for the preparation of DNA gene banks as well as for the routine subcloning of genes.

The preferred procedure for preparing competent cells of *E. coli* is based on the method of Hanahan (1983) with the following modifications: (1) the cells are grown at temperatures less than 37° C., and generally between 18° C. to 32° C. with the preferred growth temperature depending on the strain of *E. coli;* (2) sodium chloride is present in the growth medium for some *E. coli* strains; (3) sodium succinate is present in the fermentation medium, and (4) for large volumes of cells, 250 ml Corning centrifuge bottles are used for the rapid resuspension of cell pellets. Reference is made to Hanahan (1983) for details of the procedure described below.

In general, strains were stored at $-70°$ C. A few fresh colonies were innoculated into 5 ml of SOB medium (see below) and incubated with agitation until the cell density was $10^8$ to $2\times10^8$/ml. The culture was diluted 1:1 into 40% glycerol/60% SOB medium, chilled on ice, and portions taken into serially numbered screw-cap polypropylene tubes (e.g. Nunc). The cells were kept on ice for 10 min and then flash frozen in solid $CO_2$/ethanol and placed at $-70°$ C. On the day before a transformation, a tube was removed from the freezer, a clump of cells scraped up with a sterile tip, the tube replaced immediately (without thawing), and the clump of cells placed on an LM (see below) plate. Once melted, the cells were spread to isolate single cells and placed at $37°$ C. to develop colonies. Each tube was used 5 to 10 times and discarded, after which the next tube was used. A new frozen stock should be made up yearly.

Materials and Methods

Colonies were picked off a fresh streak from the frozen stock of cells (one 2.5 mm diam. colony/10 to 15 ml) and dispersed in 1 ml of SOB medium by moderate vortexing. This was used to inoculate a prerinsed SOB medium: 10 to 30 ml in a 300-ml flask, 30 to 100 ml in a 1000-ml flask, etc. The culture was incubated at $37°$ C., 275 revs/min, until the cell density was $4\times10^7$ to $7\times10^7$/ml (absorbance at 550 nm=0.45 to 0.55 for DH1; in about 2 to 2.5 h). The cells were collected into 50-ml polypropylene tubes (e.g. Falcon 2070), placed on ice for 10 to 15 min. and pelleted at 2500 revs/min for 12 min at $4°$ C. The cells were resuspended in $\frac{1}{3}$ vol. TFB by gentle vortexing, placed on ice for 10 to 15 min, and pelleted again at 2500 revs/min for 10 min at $4°$ C. The pellet was resuspended in TFB at 1/12.5 of the original volume of cells (2.5 ml of the culture is concentrated into 200 $\mu$l, one discrete transformation). Fresh DMSO was added to 3.5% (7 $\mu$l/200 $\mu$l), swirled, and left on ice for 10 min. Another equal portion of DMSO was added, and the cells incubated for 5 min. on ice. Samples (210 $\mu$l) were then placed into chilled 17 mm $\times$ 100 mm polypropylene tubes (Falcon 2059). DNA was added (in <10 $\mu$l), and the mixture swirled and incubated on ice for 30 min. The mixture was heat-pulsed without agitation at $42°$ C. for 90 s and placed on ice for 1 to 2 min. Then 800 $\mu$l of SOC medium (about $20°$ C.) was added and the tubes incubated at $37°$ C., 225 revs/min for 1 h. An appropriate fraction of the culture was pipetted in a pool of SOB medium (100 to 200 $\mu$l) on an LM plate (with appropriate antibiotic) and spread gently and minimally using a bent (L-shaped) Pasteur pipette. These plates were incubated at $37°$ C. to establish colonies. If more than 10% of the transformation was to be plated, the cells were washed and concentrated as described below.

The heat pulse has been calibrated for 17 mm $\times$ 100 mm polypropylene tubes (Falcon 2059). If other tubes are used, the length of the heat pulse should be recalibrated. For example, a scaled up transformation, in which 25 ml of cells are concentrated in 2 ml can be performed in a 50-ml polypropylene tube (Falcon 2070). In this case, the optimal time for the heat pulse is 210 s. A scaled up transformation may be concentrated and plated on two 150 mm plates or four 100 mm plates.

The comments set forth below include various conclusions and recommendations based on various techniques practiced according to the invention.

Media

S.O.B., S.O.C., and LM agar plates are defined and described by Hanahan (1983). S.O.B. with 0.5% sodium succinate is used in fermentation broths. S.O.B. and LM agar plates with sodium chloride are prepared by adding sodium chloride after the medium is autoclaved. YET ampicillin 100 agar plates are 10 g/l BactoTrytone, 5 g/l Yeast Extract, 5 g/l NaCl, and 100 ug/ml Ampicillin and 15 g/l Bactoagar.

Media and plates

All plates were LM: 1% (W/V) Bacto tryptone, 0.5% (w/v) yeast extract, 10 mM-NaCl, 10 mM-MgSO$_4$.7H$_2$O, 1.5% (w/v) Bacto agar. For tetracycline plates, the Mg$^{2+}$ was omitted. Tryptone, yeast extract and agar were from Difco Labs. All antibodies were used at 35 $\mu$g/ml, except for tetracycline, which was used at 17 $\mu$g/ml.

SOB medium is 2% (w/v) Bacto Tryptone, 0.5% (w/v) yeast extract, 10 mM-NaCl, 2.5 mM-KCl, 10 mM-MgCl$_2$. SOB medium was prepared without Mg$^{2+}$ and autoclaved. A 2M stock of Mg$^{2+}$ (1 M-MgCl$_2$.6H$_2$O+1M-MgSO$_4$.7H$_2$O, sterile filtered) was used to make the medium 20 mM in Mg$^{2+}$, after which it was sterile filtered through a prerinsed 0.22 $\mu$m filter unit. The final pH was 6.8 to 7.0.

SOC medium is SOB medium containing 20 mM-glucose, and was prepared similarly before filtration, the medium was made 20 mM in glucose using a sterile filtered 2M stock. The water used for these media was the purest available.

Buffers

F.S.B. is made as defined and described by Hanahan (1983). F.S.B. buffer containing 5% sucrose (w/v) is used when making strains DH1 and DH5 competent. S.O.B./glycerol solution (60/40 v/v) is prepared as described by Hanahan (1983).

FSB (transformation buffer for frozen storage of competent cells) is 10 mM-potassium acetate, 100 mM-KCl, 44 mM-MnCl$_2$.4H$_2$O, 10 mM-CaCl$_2$.2H$_2$O, 3 mM-HACoCl$_3$, 10% redistilled glycerol. 1M-potassium acetate is adjusted to pH 7.0, sterile filtered, and stored frozen. All salts are added as solids. The pH of the complete solution is adjusted to 6.4 with 0.1M-HCl, and the solution is sterile filtered and stored at $4°$ C.; the pH drifts downward to a final value of 6.1 to 6.2 and then stabilizes. RbCl may be required for some strains.

DNA

Monomer pBR322 plasmid DNA is used to determine the transformation efficiency of the cells. Plasmid DNA is prepared from *Escherichia coli* strain HB101/pBR322 by the use of CsCl$_2$ density gradients.

Transformation

The procedure used to determine the transformation efficiency of the competent cells is described by Hanahan (1983) as described above. Modifications of this procedure such as using 0.1 ml rather than 0.2 ml of competent cells have also been used to determine transformation efficiency of the cells.

Freeze Thaw Protocol

A 550 ul aliquot of frozen competent cells is placed on ice until the cells have thawed. The appropriate amount of cells is removed. The cells are then frozen in a dry ice ethanol ("ETOH") bath for five minutes and placed back in a −70° C. freezer until the cells are used again.

E. coli Strains

RR1: $F^-$ hsdS20 ($r_b^-, m_B^-$) supE44 ara14 galK2 lacY1 proA2 leu rpsL20 xy15m+1-1

HB101: $F^-$ hsdS20 ($r_B^-, m_B^-$) supE44 ara14 galK2 lacY1 proA2 leu rpsL20 xy1-5 m++1-1 recA13

DH1: $F^-$ endA1 hsdR17 ($r_K^-, m_K^+$) supE44 thi-1 recA1 gyrA96 relA1

DH5: $F^-$ endA1 hsdR17 ($r_K^-, m_K^+$) supE44 thi-1 recA1 gyrA96 relA1

Reagents and Equipment

All reagents should be of the highest quality available. The water used to make solutions should be of the purest quality. Milli Q water (Milli Q Corporation) is recommended (Hanahan 1983). All glassware should be extremely clean. All glassware should be rinsed with distilled water and culture flasks should be autoclaved with distilled water in them prior to use.

General Comments Concerning the Examples

Preparation of Master Seeds

Strains of *Escherichia coli* were stored as −70° C. glycerol stocks. The procedure used to make these master seeds is describe by Hanahan (1983). Cells were prepared as described above, except that FSB was used. DMSO was added twice and DTT was omitted. The cells were portioned out into 2059 tubes or screwcap polypropylene tubes (e.g., Nunc), flash-frozen in solid $CO_2$/EtOH or liquid $N_2$, and placed at −70° C. To use, tubes were removed and thawed in air at 20° C., and, when just liquid, placed on ice for 10 min. A pure source of the bacterial strain (such as an agar stab, a −70° C. glycerol stock or colonies on an agar plate) was streaked on LM agar plates and the plates were incubated at 37° C. for a period of time that resulted in colonies of 1-2 mm in diameter for generally 10 to 16 hours. Two colonies from the LM agar plates were inoculated into 1-2 mls of S.O.B. medium and vortexed. This inoculum was used to inoculate 30-50 ml of S.O.B. in a 500 ml nonbaffled flask. This culture was grown at 37° C., 200-300 RPM to an $O.D._{550}$ of 0.5-0.7. The speed of shaking should be rapid enough to give good aeration but no foaming. When the culture reached the appropriate optical density, an aliquot was removed and added to an equal volume of 60% S.O.B. and 40% glycerol (v/v) in a sterile tube. The cells were left on ice for 10 minutes. The cells were then aliquoted into sterile chilled 4° C. Nunc tubes and frozen at −70° C. in a dry ice ETOH bath for five minutes. Master seeds were stored at −70° C. These master seeds were found to be stable for over a year.

Preparation of Primary Seeds

Primary seeds are used to inoculate cultures that will serve as the inoculum for a fermentation. Primary seeds will also generate colonies for an inoculum of a shake flask. A master seed was removed from a −70° C. freezer and put on dry ice so as not to thaw. The surface of the frozen seed was scraped and frozen cells were placed on the surface of an LM agar plate or an LM NaCl agar plate. The optimal salt concentration, generally between 0-0.3M was determined for each *E. coli* strain. The pool of cells was streaked to isolate single colonies. The plates were incubated at the preferred growth temperature, generally between 18° C. and 32° C. The growth temperature for the culture used to make the primary seed is generally the temperature at which the cells will be made competent. However the primary seed can be made from a culture grown at a higher growth temperature and that primary seed can be used to prepare competent cells from a culture grown at a lower temperature.

The colonies that appeared on the LM agar plates or LM NaCl agar plates were used to inoculate a 500 ml nonbaffled shake flask with 30 to 50 ml of S.O.B. or S.O.B. NaCl (depending on the strain of *E. coli*). The shake flask culture was grown at the appropriate temperature to an $O.D._{550}$ equal to 0.7. From this culture an aliquot was removed and mixed with an equal volume of 60% S.O.B./40% glycerol. Cells were left on ice for 10 minutes and then aliquoted into sterile chilled 4° C. Nunc tubes (0.5-1.0 ml/tube). The cells were then frozen in a dry ice/ETOH bath. Primary seeds and master seeds were stored at −70° C., and it has been determined that they should be remade on a yearly basis.

Shake Flask Production of Frozen Competent Cells

A primary seed stock is used as a source of the inoculum for cultures grown in shake flasks. A primary seed was removed from a −70° C. freezer and placed on dry ice. The surface of the seed was scraped and the cells placed on an LM agar plate containing an appropriate concentration of sodium chloride. The plate was incubated at the appropriate temperature generally between 18°-32° C. according to the *E. coli* strain used. Generally the growth temperature and sodium chloride concentration are the same as used to make the primary seed. Colonies were allowed to reach a size of 1-2 mm and the colonies were picked off the plate into 1 to 2 mls of S.O.B. medium. This inoculum was used to inoculate shake flasks with a large surface to volume ratio. A good rate of shaking was found to be 250-275 rpm, the object being to obtain good mixing with as little foaming as possible. A Fernbach flask (2.8 l) containing 200 ml of S.O.B. with the appropriate amount of added sodium chloride was inoculated with an appropriate amount of the inoculum (depending on the temperature of growth). Generally cells grown between 18° C.-32° C. were found to have a doubling time which allowed for an overnight growth. The object was to obtain a culture that has an $O.D._{550}$ of 0.5±0.2. When the optimal $O.D._{550\ nm}$ was reached, the culture was poured into centrifuge bottles that could be spun at 4000 rpm and still allow for a rapid resuspension of cells. Conical centrifuge tubes made of polypropylene are preferred for this purpose. The cells were centrifuged 4000 rpm for 10 minutes at 4° C. and the cell supernate was poured off. The bottles were tapped to remove as much liquid as possible. Chilled 4° C. F.S.B. buffer was added to each cell pellet to ⅓ of the original volume, and the cells were brought into solution by tapping the bottle. After resuspension, the cells were left on ice for 15 minutes and then centrifuged at 4000 rpm at 4° C. for 10 minutes. The cell pellet was then resuspended in 1/12.5 of the original cell supernate volume using chilled 4° C. F.S.B. buffer. DMSO was added to 3.5% (v/v) and the cells were left on ice for five minutes. Another 3.5% portion of DMSO was added to the cells, and the cells were mixed and set on ice for 10 minutes. The total time for exposure of the cells to DMSO was approximately fifteen minutes. The cells were frozen in a dry ice/E-TOH bath (−70° C.) for five minutes. Aliquots of 25 mls were frozen in 50 ml polypropylene tubes, while smaller aliquots were frozen in 0.5 mls aliquots. It was found that the aliquots should be completely frozen in 5 minutes.

Fermentation Growths for Production of Frozen Competent Cells

Fermentation growths require a liquid inoculum for the fermenter. The seed culture for the fermenter is originated from a primary seed stock. The liquid culture generally is started the day before the fermenter is inoculated for cells grown at 22°–23° C., or the liquid culture is started on the day of the fermentation for cells grown at 30°–32° C. The liquid seed culture is grown using the same conditions as the culture used to make the primary seed. The liquid seed was grown to an O.D.$_{550}$ of approximately 0.1 and the liquid seed was used to inoculate a fermenter. The volume of seed culture used to inoculate the fermenter was varied from strain to strain, and had to be calibrated so that the fermentation culture reached an O.D.$_{550}$ of 1.0 at the appropriate time. The medium used in the fermentation was S.O.B. containing 5.0 g/l sodium succinate and a sodium chloride concentration determined as discussed earlier that gave the highest transformation frequency for the E. coli strain. It was found that the culture should be agitated at 300–400 rpm and aerated at 1.0–2.0 vvm. The fermentation medium should be autoclaved for 10 minutes at 121° C. and then cooled to the temperature of growth. Sodium chloride, magnesium sulfate, and magnesium chloride were added after the medium had been autoclaved and cooled. The fermentation was allowed to proceed to a final O.D.$_{550}$ of 1.0. The culture was then placed in 250 ml centrifuge bottles that allowed for easy resuspension of the cells. Cells were set on ice for five minutes and centrifuged for 10 minutes at 4° C. and 4000 rpm. The cell supernate was poured off and the cells were resuspended in 16/25 of original culture volume using chilled 4° C. F.S.B. buffer. The cells were set on ice for 15 minutes. DMSO was added to 3.5%, mixed well, and the cells were set on ice for 10 minutes. DMSO was added again to 3.5% and the cells were left on ice for five minutes. It was found that the process should be completed as rapidly as possible, i.e. from 1 to 1.25 hours in order to process 1500 ml of a culture. It was concluded that the cells should then be frozen in a dry ice/ETOH bath as 25 ml bulk portions or as small aliquots. Freezing should be rapid enough to allow for complete freezing in five minutes for the 25 ml bulk portions.

EXAMPLE 1

A primary seed of Escherichia coli strain RR1 prepared from a culture grown at 23° C. in S.O.B. and 0.3M NaCl was streaked on LM 0.3M NaCl agar plates. The plates were incubated at 23° C. for approximately 36 hours or until colonies of 1–2 mm in size were reached. Twenty colonies from these plates were picked into 2.0 ml S.O.B. with a sterile wooden applicator stick. The inoculum was vortexed and 2 mls were added to 200 ml of S.O.B. and 0.3M NaCl in a 2.8 liter nonbaffled Fernbach flask. The flask was shaken at 275 rpm at 22° C.–23° C. for about 15 to 20 hours until an O.D.$_{550}$ of 0.5 was reached. Two fifty ml aliquots were placed in chilled 4° C. 50 ml Corning tubes. The Corning tubes were placed on ice for 5–10 minutes. The tubes were spun at 2000 rpm, 4° C. for 10 minutes. The supernate was poured off, 16.7 ml of chilled 4° C. F.S.B. were added to resuspend the cells and the tubes were placed on ice for 15 minutes. The tubes were then spun as above and the cells resuspended in 4 ml of chilled 4° C. F.S.B. buffer. 0.140 ml of DMSO were added to the cells, mixed well and the tubes were set on ice for 10 minutes. 0.140 ml DMSO was added again and the tubes were left on ice for five minutes. Two 0.5 mls aliquots of cells were frozen in a dry ice/ETOH bath. The remaining nonfrozen cells (200 ul) were used for a transformation assay with 50 pg pBR322 plasmid DNA and the transformed cells were plated on YET Ampicillin 100 agar plates. The frozen cells were thawed and 200 ul of the cells were transformed as above with 50 pg pBR322 plasmid DNA. All plates were incubated at 37° C. for 24 hours. The results are given in Table 1 (lines 1 and 2).

A primary seed of strain RR1 was also used as a source of bacteria for growing the cells at 37° C. and making them competent. The primary seed was streaked on LM+0.3M NaCl agar plates and the plates were incubated at 37° C. for approximately 16 hours. Twenty colonies were picked into 2 ml of S.O.B. and vortexed. The 2 ml was used to inoculate 200 ml S.O.B. and 0.3M NaCl in a 2.8 liter nonbaffled Fernbach flask. The cells were grown at 37° C., 275 rpm to an O.D.$_{550}$ of 0.5 and made competent by the same procedure discussed above. The frozen cells were thawed and transformed with 50 pg pBR322 plasmid DNA. Cells that were not frozen were also transformed with 50 pg pBR322 plasmid DNA. Transformants are selected using YET Ampicillin 100 agar plates. The results are given in Table 1 (lines 3,4).

TABLE 1

The Effect of Growth Temperature and Freezing on the Transformation Efficiency of E. coli Strain RR1

| Growth Temperature | Cells Frozen | Ampicillin Resistant Transformants/ug pBR322 DNA |
|---|---|---|
| 23° C. | Yes | $4.2 \times 10^8 - 3 \times 10^9$ |
| 23° C. | No | $4.0 \times 10^7 - 1 \times 10^8$ |
| 37° C. | Yes | $3.0 \times 10^7 - 5 \times 10^7$ |
| 37° C. | No | $2.4 \times 10^7 - 5 \times 10^7$ |

By comparing lines 1 and 2, it is concluded that freezing cells grown at 23° C. results in an increased transformation efficiency compared to cells grown at 23° C. and not frozen. In addition RR1 cells grown at 37° C. either frozen or not frozen (lines 3 and 4) are less competent than cells grown at 23° C. and frozen. Therefore high transformation efficiencies are achieved by growth of the RR1 cells at 23° C. and the subsequent freezing of the cells.

RR1 cells grown at either 23° C. or 37° C. were frozen and thawed according to the procedure in the materials and methods section. 200 ul samples of the cells were transformed with 50 pg pBR322 plasmid DNA. The transformed cells were plated on YET ampicillin 100 agar plates. The results are presented in Table 2.

TABLE 2

Freeze Thaw Cycle vs. Transformation
Efficiency for E. coli Strain RR1 Grown at
23° C. and 37° C.

| Freeze/Thaw Cycle | Ampicillin Resistant Transformants/ug pBR322 DNA | |
|---|---|---|
| | Cells grown at 23° C. | Cells grown at 37° C. |
| 1 | $8.0 \times 10^8$ | $4.6 \times 10^7$ |
| 2 | $6.7 \times 10^8$ | $2.0 \times 10^6$ |
| 3 | $8.3 \times 10^8$ | $<1 \times 10^6$ |
| 4 | $5.7 \times 10^8$ | $<1 \times 10^6$ |
| 5 | $7.4 \times 10^8$ | $<1 \times 10^6$ |

Cells grown at low temperatures are capable of undergoing repeated freeze thaw cycles without significant loss of transformation efficiency whereas cells grown at 37° C. cannot undergo the freeze thaw cycles without loss of transformation efficiency.

EXAMPLE 2

A primary seed of E. coli strain DH5 derived from a culture grown at 30° C. with no sodium chloride was removed from the freezer and allowed to thaw at room temperature. The primary seed was diluted to 1/10 in S.O.B. and 0.1-0.3 ml was added to 50 mls of S.O.B. in a 500 ml nonbaffled shake flask. The flask was inoculated at about 9:00 A.M. on the day of the fermentation. The culture was allowed to grow at 30° C. to an $O.D._{550}$ equal to 0.1 and 0.2 ml of a 1/10 dilution was used to inoculate a 10 liter fermenter containing S.O.B. and 0.5% sodium succinate pH 7.0. The fermenter was stirred at 300 RPM, and aerated at 1 vvm. The fermenter was inoculated such that it reached an $O.D._{550}$ of 1.0, on the following day. On the following day when the fermenter reached an $O.D._{550}$ equal to 1.0, the cells were removed into sterile, chilled 4° C. 250 ml Corning bottles. Twelve bottles were filled and placed on ice for five minutes. The Corning bottles were spun 4000 rpm, 4° C. for 10 minutes. The cell supernate was poured off, excess liquid was drained and 40 mls of chilled 4° C. FSB buffer were added. The bottles were left on ice for 15 minutes. 1.4 mls of DMSO was added, the cells were mixed and then left on ice for 10 minutes. Another 1.4 mls portion of DMSO was added and the bottles were set on ice for five minutes. The twelve 40 ml aliquots of cells were mixed, aliquoted into 25 ml portions in 50 ml polypropylene tubes, and the tubes were frozen at $-70°$ C. for five minutes. A convex knob of F.S.B. appeared at the surface of the 25 ml aliquots. The results of a transformation assay using 200 ul of cells and 50 pg of pBR322 plasmid DNA indicated that the cells were competent at $1.3 \times 10^9$ transformants/ug pBR322 plasmid DNA.

EXAMPLE 3

A primary seed of E. coli strain RR1 was streaked on LM agar plates and the plates were incubated at 37° C. for 16 hours. Twenty colonies were picked into 2 mls of S.O.B. and 0.3M NaCl. The cells were inoculated into 200 mls of S.O.B. and 0.3M NaCl in a 2.8 liter nonbaffled Fernbach flask. The cells were grown at 37° C. and shaken at 275 rpm to a final $O.D._{550}$ of 0.25. The flask was placed in an ice bath and cooled to approximately 23° C. A 30 ml sample of cells was removed and the cells were made competent according to the procedure given in Example 1. The flask was then shaken at 23° C. and at 275 rpm for two hours. At 30 minute intervals, 30 ml samples were removed and the cells made competent according to the procedure given in Example 1. 200 ul portions of each sample were transformed with 50 pg PBR322 plasmid DNA. Transformants were selected on YET Ampicillin 100 agar plates and counted after the plates had been incubated at 37° C. for 24 hours. The results are presented in Table 3.

TABLE 3

Transformation Efficiency: Effect of
37° C. to 23° C. Temperature Shift on
E. coli Strain RR1

| Time After Temperature Shift to 23° C. (minutes) | Ampicillin Resistant Transformants/ug pBR322 Plasmid DNA |
|---|---|
| 0 | $7 \times 10^6$ |
| 30 | $1.1 \times 10^7$ |
| 60 | $4.0 \times 10^7$ |
| 90 | $9.9 \times 10^7$ |
| 120 | $4.6 \times 10^8$ |

The results of this experiment indicate that shifting strain RR1 from 37° C. to 23° C. for two hours results in a 60 fold increase in the efficiency of transformation compared to a sample which does not undergo a temperature shift.

We claim:

1. A process for producing transformable E. coli cells of improved competence by a process comprising the following steps in order:
    (a) growing E. coli cells in a growth-conducive medium at a temperature of 18° C. to 32° C.;
    (b) rendering said E. coli cells competent; and
    (c) freezing the cells.

2. The process according to claim 1 wherein the cells are E. coli cells having competency for plasmid DNA.

3. The process according to claim 1 wherein the cells are E. coli cells of at least one of the following strains: RR1, HB101, DH1, DH5.

4. The process according to claim 1 wherein the growth conducive medium is a complex medium containing Mg.

5. The process according to claim 1 wherein the cells are E. coli, the step of growing the cells includes growing the cells within the range 18° C. to 32° C. for a period within a range of from 1 to 20 hours.

6. The process according to claim 1 wherein the cells are E. coli, the step of growing the cells includes growing the cells in the range of 18° C. to 32° C. until the optical density at 550 nm reaches the range of 0.5 to 1.0.

7. The process according to claim 1 and further including the step of washing the cells in a buffer prior to the freezing step.

8. The process according to claim 1 wherein the cells are E. coli, and the step of freezing the cells comprises freezing the cells at approximately $-70°$ C.

9. The process according to claim 1 wherein the cells are E. coli, and the step of freezing the cells comprises freezing the cells in a dry ice-ethanol bath at approximately $-70°$ C.

10. The process according to claim 1 and further including the step of storing the cells at $-70°$ C. after the freezing step.

11. The process according to claim 1 wherein the cells are E. coli, and the step of growing the cells includes growing the cells in the presence of sodium chloride.

12. The process according to claim 1 wherein the cells are E. coli, and the step of growing the cells includes growing the cells in the presence of sodium succinate.

13. The process according to claim 1 and further including the steps of thawing and refreezing the cells after said freezing step.

14. The process according to claim 1, wherein the process further comprises the following step between step (a) and step (b):
 (a') harvesting the cells by centrifugation.

15. The process according to claim 14, wherein the process further comprises the following step between step (a') and step (b):
 (a") rapidly resuspending the cells in an appropriate buffer.

16. The process of claim 1, wherein said E. coli are rendered competent in step (b) by washing the cells with a buffer comprising potassium acetate, KCl, $MnCl_2.4H_2O$, $CaCl_2.2H_2O$, hexamine cobalt chloride and redistilled glycerol.

17. Transformable *E. coli* cells of improved competence produced by the following steps in order:
 (a) growing *E. coli* cells in a growth-conducive medium at a temperature of 18° C. to 32° C.;
 (b) rendering said *E. coli* cells competent; and
 (c) freezing the cells.

18. The competent transformable cells according to claim 17 wherein the cells are *E. coli* having a competency for plasmid DNA, and a transformation efficiency of at least $1 \times 10^9$ transformants per microgram of plasmid DNA.

19. The competent transformable cells according to claim 17 wherein the cells are *E. coli* having high transformation efficiencies, and are made by the further steps of repeatedly thawing and freezing the cells after said freezing step without significantly diminishing the transformation efficiencies.

20. The competent transformable cells according to claim 17 wherein the cells are frozen competent *E. coli* strain RR1.

21. The competent transformable cells according to claim 17 wherein the cells are frozen competent *E. coli* strain HB101.

22. The competent transformable cells according to claim 17 wherein the cells are frozen competent *E. coli* strain DH1.

23. The competent transformable cells according to claim 17 wherein the cells are frozen competent *E. coli* strain DH5.

24. The competent transformable *E. coli* cells of claim 17, wherein said *E. coli* are rendered competent in step (b) by washing the cells in a buffer comprising potassium acetate, KCl, $MnCl_2.4H_2O$, $CaCl_2.2H_2O$, hexamine cobalt chloride and redistilled glycerol.

* * * * *